(12) United States Patent
Billodeaux et al.

(10) Patent No.: US 9,315,485 B2
(45) Date of Patent: *Apr. 19, 2016

(54) PRODUCTION OF CYCLIC ACETALS BY REACTIVE DISTILLATION

(71) Applicant: Eastman Chemical Company, Kingsport, TN (US)

(72) Inventors: Damon Ray Billodeaux, Raleigh, NC (US); Robert Scott Huss, Kingsport, TN (US); Daniel Latham Terrill, Bristol, TN (US); Jerome Leonard Stavinoha, Jr., Longview, TX (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/459,875

(22) Filed: Aug. 14, 2014

(65) Prior Publication Data

US 2014/0357875 A1    Dec. 4, 2014

Related U.S. Application Data

(63) Continuation of application No. 13/168,229, filed on Jun. 24, 2011, now Pat. No. 8,829,207.

(51) Int. Cl.
   *C07D 319/06* (2006.01)
   *C07D 317/12* (2006.01)

(52) U.S. Cl.
   CPC ............ *C07D 319/06* (2013.01); *C07D 317/12* (2013.01)

(58) Field of Classification Search
   CPC .................................................... C07D 319/06
   See application file for complete search history.

(56) References Cited

U.S. PATENT DOCUMENTS

| | | | |
|---|---|---|---|
| 2,425,042 A | 8/1947 | McNamee et al. |
| 2,429,878 A | 10/1947 | Gresham et al. |
| 2,486,024 A | 10/1949 | Hearne et al. |
| 3,275,680 A | 9/1966 | Holzrichter et al. |
| 4,024,159 A | 5/1977 | Peterson |
| 4,038,175 A | 7/1977 | Bhasin |
| 4,062,898 A | 12/1977 | Dubeck et al. |
| 4,071,568 A | 1/1978 | Onoda et al. |
| 4,088,700 A | 5/1978 | Watts |
| 4,169,959 A | 10/1979 | Arpe |
| 4,308,403 A | 12/1981 | Knifton |
| 4,317,943 A | 3/1982 | Knifton |
| 4,356,327 A | 10/1982 | Knifton |
| 4,357,477 A | 11/1982 | Knifton |
| 4,375,394 A | 3/1983 | Devon |
| 4,390,734 A | 6/1983 | Knifton |
| 4,430,253 A | 2/1984 | Dubeck |
| 4,435,595 A | 3/1984 | Agreda et al. |
| 4,478,017 A | 10/1984 | Brown et al. |
| 4,479,017 A | 10/1984 | Ayusawa et al. |
| 4,482,753 A | 11/1984 | Tai-Huang et al. |
| 4,484,009 A | 11/1984 | Ghenassia et al. |
| 4,537,980 A | 8/1985 | Greenshields |
| 4,568,780 A | 2/1986 | Knifton |
| 4,617,287 A | 10/1986 | Lyons |
| 4,618,729 A | 10/1986 | Duggan et al. |
| 4,663,489 A | 5/1987 | Duggan et al. |
| 4,692,426 A | 9/1987 | Duggan et al. |
| 4,847,425 A | 7/1989 | Degner et al. |
| 4,895,818 A | 1/1990 | Duggan et al. |
| 4,895,987 A | 1/1990 | Duggan et al. |
| 4,939,294 A | 7/1990 | Agreda et al. |
| 5,319,148 A | 6/1994 | Karcher et al. |
| 5,362,918 A | 11/1994 | Aizawa et al. |
| 5,399,631 A | 3/1995 | Egawa et al. |
| 5,446,208 A | 8/1995 | Koshino et al. |
| 5,446,210 A | 8/1995 | Hees et al. |
| 5,523,491 A | 6/1996 | Egawa et al. |
| 5,589,597 A | 12/1996 | Egawa et al. |
| 5,616,736 A | 4/1997 | Thigpen |
| 5,720,895 A | 2/1998 | Nakagawa et al. |
| 5,763,691 A | 6/1998 | Kawabe et al. |
| 5,780,687 A | 7/1998 | Holderich et al. |
| 5,821,391 A | 10/1998 | Holderich et al. |
| 5,866,735 A | 2/1999 | Cheung |
| 5,886,198 A | 3/1999 | Ogawa et al. |
| 5,917,059 A | 6/1999 | Bruchmann et al. |
| 5,935,896 A | 8/1999 | Dupuis et al. |
| 6,013,844 A | 1/2000 | Heineke et al. |
| 6,015,875 A | 1/2000 | Smith et al. |
| 6,028,215 A | 2/2000 | Bessling et al. |

(Continued)

FOREIGN PATENT DOCUMENTS

| CA | 1 254 190 | 5/1989 |
|---|---|---|
| DE | 419223 C | 9/1925 |

(Continued)

OTHER PUBLICATIONS

Knifton "Syngas reactions: Part VIII: The preparation of glycol monoalkyl ethers," Journal of Molecular Catalysis 1985, 30, pp. 281-297.

Jakab et al. "Synthesis, regioselective hydrogenolysis, partial hydrogenation, and conformational study of dioxane and dkoxane-type (9-anthracenyl)methylene acetals of sugars," Carbohydrate Research 2009, 344, pp. 2444-2453.

Broekhuis et al. "Recovery of Propylene Glycol from Dilute Aqueous Solutions via Reversible Reaction with Aldehydes" Ind. Eng. Chem. Res. 1994, 33, pp. 3230-3237.

(Continued)

*Primary Examiner* — Golam M M Shameem
*Assistant Examiner* — Laura Daniel
(74) *Attorney, Agent, or Firm* — Phan Law Group PLLC

(57) ABSTRACT

Cyclic acetals can be produced in a reactive distillation apparatus by combining a polyhydroxyl compound and an aldehyde. High concentrations of cyclic acetals are removed as liquid products from the column while water is removed as an overhead vapor stream.

4 Claims, 1 Drawing Sheet

(56) References Cited

U.S. PATENT DOCUMENTS

| | | | |
|---|---|---|---|
| 6,080,897 A | 6/2000 | Kawabe | |
| 6,087,539 A | 7/2000 | Yamasaki et al. | |
| 6,124,479 A | 9/2000 | Hinoue et al. | |
| 6,136,576 A | 10/2000 | Diaz-Torres | |
| 6,143,908 A | 11/2000 | Hinoue et al. | |
| 6,166,240 A | 12/2000 | Jiang et al. | |
| 6,207,850 B1 | 3/2001 | Jiang et al. | |
| 6,232,512 B1 | 5/2001 | Haas et al. | |
| 6,265,623 B1 | 7/2001 | Morawietz et al. | |
| 6,291,725 B1 | 9/2001 | Chopade | |
| 6,380,419 B2 | 4/2002 | Kawabe | |
| 6,458,992 B1 | 10/2002 | Lederer et al. | |
| 6,518,464 B2 | 2/2003 | Therre et al. | |
| 6,548,681 B1 | 4/2003 | Chopade et al. | |
| 6,657,089 B1 | 12/2003 | Nagasawa et al. | |
| 6,670,489 B2 | 12/2003 | Koyama et al. | |
| 6,713,640 B2 | 3/2004 | Miller et al. | |
| 6,969,779 B2 | 11/2005 | Brewer et al. | |
| 7,030,277 B2 | 4/2006 | Groten et al. | |
| 7,060,372 B2 | 6/2006 | Fryd et al. | |
| 7,071,362 B2 | 7/2006 | Sugawara et al. | |
| 7,160,524 B2 | 1/2007 | Lederer et al. | |
| 7,301,055 B2 | 11/2007 | Hoffmockel et al. | |
| 7,321,052 B2 | 1/2008 | Miller et al. | |
| 7,488,851 B2 | 2/2009 | Rodrigues et al. | |
| 7,498,451 B2 | 3/2009 | Haderlein et al. | |
| 7,534,922 B2 | 5/2009 | Gorling et al. | |
| 7,754,900 B2 | 7/2010 | Siegert et al. | |
| 8,785,697 B2 | 7/2014 | Billodeaux et al. | |
| 8,829,206 B2 | 9/2014 | Terrill et al. | |
| 8,829,207 B2 | 9/2014 | Billodeaux et al. | |
| 9,056,313 B2 | 6/2015 | Devon et al. | |
| 2003/0187281 A1 | 10/2003 | Miller et al. | |
| 2006/0129000 A1 | 6/2006 | Goring et al. | |
| 2008/0283384 A1 | 11/2008 | Lang et al. | |
| 2010/0048940 A1 | 2/2010 | Tulchinsky et al. | |
| 2010/0099894 A1 | 4/2010 | Dubois et al. | |
| 2010/0158780 A1 | 6/2010 | Galligan et al. | |
| 2010/0228065 A1 | 9/2010 | Cheung et al. | |
| 2010/0261936 A1 | 10/2010 | Okumura et al. | |
| 2010/0292491 A1 | 11/2010 | Selifonov et al. | |
| 2011/0034739 A1 | 2/2011 | Stochniol et al. | |
| 2011/0207969 A1 | 8/2011 | Olken et al. | |
| 2012/0121911 A1* | 5/2012 | Mullen | C07D 317/30 428/412 |
| 2012/0330032 A1 | 12/2012 | Terrill et al. | |
| 2012/0330033 A1 | 12/2012 | Terrill et al. | |
| 2012/0330034 A1 | 12/2012 | Billodeaux et al. | |
| 2012/0330066 A1 | 12/2012 | Devon et al. | |
| 2012/0330067 A1 | 12/2012 | Devon et al. | |
| 2012/0330069 A1 | 12/2012 | Billodeaux et al. | |
| 2014/0330029 A1 | 11/2014 | Terrill et al. | |

FOREIGN PATENT DOCUMENTS

| | | |
|---|---|---|
| DE | 3328561 A1 | 2/1985 |
| DE | 238 232 A1 | 8/1986 |
| DE | 19648960 A1 | 5/1998 |
| DE | 10036423 A1 | 3/2001 |
| EP | 0 168 989 A1 | 1/1986 |
| EP | 0 169 666 B1 | 1/1986 |
| EP | 0 271 091 A1 | 6/1988 |
| EP | 0 312 659 A1 | 4/1989 |
| EP | 0499055 A2 | 8/1992 |
| EP | 0616994 A2 | 9/1994 |
| EP | 0624563 A1 | 11/1994 |
| EP | 0696564 A1 | 2/1996 |
| EP | 1 236 511 A1 | 9/2002 |
| FR | 2 906 246 A1 | 3/2008 |
| GB | 1020500 A | 2/1966 |
| GB | 1046608 A | 10/1966 |
| JP | 52073810 A | 6/1977 |
| JP | 56166186 A | 12/1981 |
| JP | 58198431 A | 11/1983 |
| JP | 5155878 A | 6/1993 |
| JP | 5271217 A | 10/1993 |
| JP | 6128184 A | 5/1994 |
| JP | 7-224055 A | 8/1995 |
| JP | 2001-031671 A | 2/2001 |
| JP | 2001072636 A | 3/2001 |
| JP | 4287546 B2 | 7/2009 |
| WO | WO 01/19763 A1 | 3/2001 |
| WO | WO 03/002547 A1 | 1/2003 |
| WO | WO 2010/027663 A1 | 3/2010 |

OTHER PUBLICATIONS

Dhale et al. "Propylene Glycol and Ethylene Glycol Recovery from Aqueous Solution via Reactive Distillation" Chemical Engineering Science, 2004, 59, pp. 2881-2890.

Hao et al. "Downstream processing of 1,3-propanediol fermentation broth" J. Chem. Technol. Biotechnol. 2006, 81, pp. 102-108.

Howard et al. "Hydrogenolysis of Ketals" J. Org. Chem., 1961 26(4), pp. 1026-1028.

Osman et al. "Cyclic Acetal Formation Between 2-Pyridinecarboxaldehyde and y-Hydroxy-a,b-Acetylenic Esters" Tetrahedron Lett. 2008, 49 (46) pp. 6550-6552.

Zajac et al. "Reaction of 2-Butynal Diethyl Acetal with Lithium Aluminum Hydride" J. Org. Chem., 1975 40(4), pp. 530-531.

Astle et al. "Catalysis with Cation-Exchange Resins, Preparation of 1,3 Dioxolanes and 1,3,6-Trioxocanes", Industrial and Engineering Chemistry, Apr. 1954, pp. 787-791.

Singh et al. "Production of Butyl Acetate by Catalytic Distillation. Theoretical and Experimental Studies" Ind. Eng. Chem. Res. 2005, 44, pp. 3042-3052.

Venimadhavan et al. "A Novel Distillate Policy for Batch Reactive Distillation with Application to the Production of Butyl Acetate" Ind. Eng. Chem. Res. 1999, 38, pp. 714-722.

Chadda et al. "Feasibility and Synthesis of Hybrid Reactive Distillation Systems" AIChE Journal, Dec. 2002, vol. 48, No. 12, pp. 2754-2768.

Sulzbacher et al., J. Am. Chem. Soc. 1948, 70(8), pp. 2827-2828.

Bronsted and Grove, J. Am. Chem. Soc. 1930, 52(4), pp. 1394-1403.

Van Duzee et al., J. Am. Chem. Soc. 1935, 57, p. 147.

Bonner et al., J. Am. Chem. Soc., Perkins Trans. 1981, pp. 1807-1810.

Tkachenko et al. "Research in the Field of Furan Acetal Compounds. XII. Features of the Vapor-Phase Hydrogenation of Disubstituted 1,3-Dioxolanes", Chemistry and Technology of Furan Compounds, 1985, pp. 59-64.

Public Dow literature, "Dow Technology Licensing—METEOR™ Ethylene Oxide/Glycol Process Technology," http://www.dow.com/licensing/offer/meteor.htm (downloaded and printed from the internet on Aug. 24, 2011).

Public Shell literature, "Factsheets: OMEGA and ethylene oxide/ethylene glycol technology," http://www.shell.com/home/content/chemicals/aboutshell/media_centre/factsheets/omega/ (downloaded and printed from the internet on Aug. 24, 2011).

Public website at http://globalbiochemna.com/, Global BioChem Technology Group (GBT), Product Information, "About Us, and Glycols Project/Polyol Chemicals" (downloaded and printed from the internet on Aug. 24, 2011).

Public Dow literature, Dow Product Safety Assessment, "Ethylene Glycol Butyl Ether" (EGBE), at http://www.dow.com/productsafety, Product Safety Assessment Finder. (downloaded and printed from the internet on Aug. 24, 2011).

Kul'nevich et al., Khimiya Geterotsiklicheskikh Soyedinenii, No. 8, 1977, pp. 1026-1029.

Coelho, Antonio Carlos Vieira, et al.; "Surface Area, Crystal Morphology and Characterization of Transition Alumina Powders from a New Gibbsite Precursor"; Materials Research, vol. 10, No. 2, pp. 183-189, (2007), XP002683656.

Hudson, L. Keith, et al.; "Aluminum Oxide", Internet Citation XP-002596245, pp. 1-40, Jun. 15, 2000, URL: http://onlinelibrary.wiley.com/doi/10.

Luyben, William L., et al.; "Reactive Distillation Design and Control", John Wiley & Sons, 2008, p. 514-517.

Hibbert, H., et al.: Studies on the reactions relating to carbohydrates and polysaccharides. X. Synthesis and relative stability of cyclic

(56) References Cited

OTHER PUBLICATIONS acetals from 1, 2- and 1, 3-glycols; Journal of the American Chemistry Society, vol. 46, No. 5, 1924. pp. 1283-1290, XP002621973, pp. 1286, 1287, "Experimental Part".
Stichlmair, Johann, et al.; "Reactive Distillation Processes"; Chemical Engineering Technology, 22 (1999) 2; pp. 95-103.
Notification of Transmittal of the International Search Report and the Written Opinion of the International Searching Authority dated Jun. 19, 2012 for International Application No. PCT/US2012/043085.
Notification of Transmittal of the International Search Report and the Written Opinion of the International Searching Authority dated Jun. 14, 2012 for International Application No. PCT/US2012/042378.
Notification of Transmittal of the International Search Report and the Written Opinion of the International Searching Authority dated Jun. 8, 2012 for International Application No. PCT/US2012/041459.
Notification of Transmittal of the International Search Report and the Written Opinion of the International Searching Authority dated Sep. 3, 2012 for International Application No. PCT/US2012/042458.
Notification of Transmittal of the International Search Report and the Written Opinion of the International Searching Authority dated Sep. 11, 2012 for International Application No. PCT/US2012/043071.
Notification of Transmittal of the International Search Report and the Written Opinion of the International Searching Authority dated Oct. 15, 2012 for International Application No. PCT/US2012/042453.
Notification of Transmittal of the International Search Report and the Written Opinion of the International Searching Authority dated Sep. 14, 2012 for International Application No. PCT/US2012/043093.
USPTO Office Action dated Nov. 9, 2012 for co-pending U.S. Appl. No. 13/168,374.
USPTO Office Action dated May 21, 2013 for co-pending U.S. Appl. No. 13/168,374.
USPTO Office Action dated Nov. 1, 2013 for co-pending U.S. Appl. No. 13/168,274.
USPTO Office Action dated Nov. 1, 2013 for co-pending U.S. Appl. No. 13/168,304.
USPTO Office Action dated Nov. 1, 2013 for co-pending U.S. Appl. No. 13/168,349.
USPTO Notice of Allowance dated Jun. 3, 2014 for co-pending U.S. Appl. No. 13/168,374.
USPTO Office Action dated Jun. 4, 2014 for co-pending U.S. Appl. No. 13/168,304.
USPTO Office Action dated Jun. 5, 2014 for co-pending U.S. Appl. No. 13/168,349.
Copending U.S. Appl. No. 14/307,956, filed Jun. 18, 2014; Damon Ray Billodeaux et al.
USPTO Office Action dated Jul. 2, 2014 for co-pending U.S. Appl. No. 13/168,274.
USPTO Notice of Allowance dated Jul. 7, 2014 for co-pending U.S. Appl. No. 13/168,374.
English translation of FR 2 906 246 A1, pp. 1-13, (Mar. 28, 2008).
USPTO Notice of Allowance dated Dec. 19, 2014 for co-pending U.S. Appl. No. 13/168,374.
USPTO Notice of Allowance dated Feb. 25, 2015 for co-pending U.S. Appl. No. 13/168,274.
USPTO Notice of Allowance dated Apr. 21, 2015 for co-pending U.S. Appl. No. 13/168,349.
USPTO Office Action dated May 7, 2015 for co-pending U.S. Appl. No. 14/337,544.
USPTO Office Action dated Jan. 29, 2016 for co-pending U.S. Appl. No. 14/605,067.
V.I. Stenberg et al., "Catalytic Dehydrator. A Simplified Isolation Procedure for Acetals and Ketals," J. Org. Chem., vol. 39, pp. 2815-2816 (1974).
USPTO Office Action dated Nov. 18, 2015 for co-pending U.S. Appl. No. 14/337,544.
USPTO Office Action dated Dec. 11, 2015 for co-pending U.S. Appl. No. 14/168,304.
USPTO Office Action dated Jun. 25, 2015 for co-pending U.S. Appl. No. 13/168,304.
USPTO Office Action dated Sep. 2, 2015 for co-pending U.S. Appl. No. 14/307,956.

\* cited by examiner

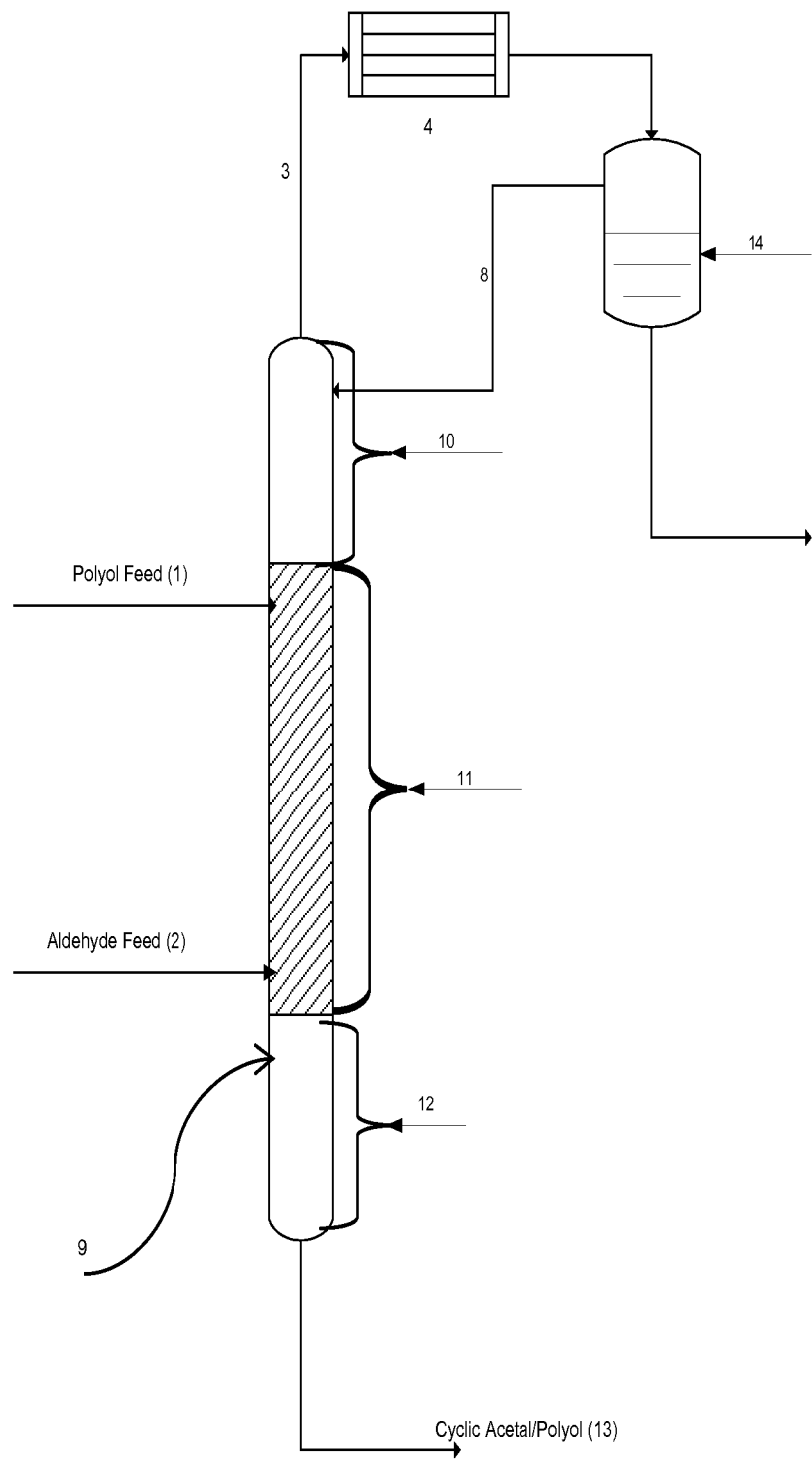

PRODUCTION OF CYCLIC ACETALS BY REACTIVE DISTILLATION

CROSS-REFERENCES TO RELATED APPLICATIONS

This application is a Continuation of U.S. application Ser. No. 13/168,229 filed Jun. 24, 2011, the contents of which are incorporated by reference in their entirety herein.

FIELD OF THE INVENTION

The invention relates to the production of cyclic acetals in high yield by reactive distillation and compositions containing high yields of cyclic acetals.

BACKGROUND OF THE INVENTION

Ether alcohols, such as 2-butoxyethanol, have important industrial functions in such products such as cleaning supplies and coating materials. In the past, the manufacture of these products has been based on a process relying on a reaction between an alcohol and ethylene oxide. This conventional process has proven to be somewhat inefficient, in that it produces various undesirable byproducts along with the ether alcohols.

Monoether glycols can also be manufactured in a process dependent on aldehydes and a polyhydroxyl compound, instead of ethylene oxide, as starting materials. In such processes cyclic acetals are first generated. The acetal of ethylene glycol and butyraldehyde, for example, is described by Hibbert and Timm (Hibbert, H.; Timm, J. A. *J. Am. Chem. Soc.* 1924, 46(5), 1283-1290.) and is achieved with a maximum yield of 50% under acidic conditions. These cyclic acetals can then be subjected to hydrogenolysis in the presence of palladium and phosphoric acid catalysts. Such a process is described in U.S. Pat. No. 4,484,009.

The reaction of the polyhydroxyl compounds with aldehydes is an equilibrium reaction with the acetal product and co-product water. Yield of acetal is reduced via hydrolysis of the acetal by the co-product water. Thus, it is desirable to remove water from the reaction system to increase yield of the acetal.

The separation of water from the reaction mixture has been difficult since it often forms an azeotrope with the aldehyde reactants and with the cyclic acetal products. Entrainers have been employed to remove water through azeotropic distillation. Sulzbacher and coworkers, for example, describe removing the water by using benzene during the preparation of a number of acetals of ethylene glycol (Sulzbacher, M. et. al. *J. Am. Chem. Soc.* 1948, 70(8), 2827-2828). The environmental and health impact of benzene is an obvious concern in this method. Desiccants such as calcium chloride (DE 419223; Brönsted and Grove *J. Am. Chem. Soc.* 1930, 52(4), 1394-1403) may be employed in the reaction vessel to remove water as it is formed, but disposal of the generated solid waste is an economic and environmental concern.

Another method as described by Astle and coworkers, involves heating the glycol and aldehyde in a batch process over an heterogeneous acidic resin and distilling out in an overhead stream the acetal and water as they are formed (Astle, M. J. et al, *Ind. Eng. Chem.* 1954, 46(4), 787-791). This method generates high yields, but catalyst lifetime, cost, and the economic impact of multiple reaction vessels is a drawback.

In U.S. Pat. No. 5,917,059 to BASF Aktiengesellschaft, the authors generated cyclic acetals and ketals by reacting a molar excess of aldehydes and ketones with polyhydroxyl compounds in the presence of an acid catalyst. The water is removed by continuously distilling unreacted aldehydes or ketone starting materials, thus co-distilling the formed water in the water/aldehyde azeotrope, and further replacing the distilled aldehyde or ketone with fresh aldehyde or ketone. The aldehydes and ketones act not only as a reactant but also as a medium for transporting the water produced in the reaction. This method requires large excess of aldehyde (e.g. 4:1 molar ratio of aldehyde: alcohol) to be successful.

Reactive distillation is employed in U.S. Pat. No. 6,015,875 and U.S. Pat. No. 7,534,922 B2 to generate low boiling acetals. The authors make use of heterogeneous acids in the packing of the column and feed low boiling starting materials such as methanol, ethanol, formaldehyde, and acetaldehyde. The formed acetals are removed overhead above the distillation reaction zone and the co-product water is removed below the distillation reaction zone. This method limits the types of usable reactants to those producing materials that boil at a temperature lower than water.

SUMMARY OF THE INVENTION

In accordance with one embodiment of the present invention, there is provided a process for the production of a cyclic acetal in a reactive distillation column comprising:
(a) feeding to the column polyhydroxyl compounds and aldehyde compounds,
(b) reacting the polyhydroxyl compounds with the aldehyde compounds in a reaction zone in the column to form a reaction mixture comprising liquid cyclic acetal compounds and water as a co-product, and
(c) withdrawing from the column one or more product streams comprising cyclic acetal compounds, and
(d) withdrawing from the column an overhead vapor stream rich in concentration of water co-product relative to any one of the product streams, wherein the concentration of cyclic acetals in each of the product streams is greater than the concentration of cyclic acetal compounds in the overhead vapor stream, and
(e) separating cyclic acetal compounds from the product stream and thereafter isolating the cyclic acetal compounds to form a purified cyclic acetal compound stream comprising at least 80 mole % of cyclic acetals based on the moles of all ingredients in the purified cyclic acetal compounds stream.

In another embodiment of the invention, there is provided a process for preparing a cyclic acetal comprising:
(i) reacting in a distillation column a stoichiometric molar excess of a polyhydroxyl compounds with aldehyde compounds to produce a liquid reaction mixture comprising cyclic acetal compounds and unreacted polyhydroxyl compounds, and
(ii) separating in a distillation column at least a portion of the liquid cyclic acetal compounds from the reaction mixture.

The process of the invention can attain high conversion rates of aldehyde compounds in amounts of at least 80%.

The process of the invention can also attain high selectivity to the production of cyclic acetal compounds in amount of at least 80%.

BRIEF DESCRIPTION OF THE DRAWING FIGURE

FIG. 1 is a process flow diagram illustrating a reactive distillation column in which the product stream containing desired cyclic acetals is removed as a bottoms stream.

DETAILED DESCRIPTION OF THE INVENTION

As used in the description of the invention, "compounds" which modify an aldehyde, a polyhydroxyl, or an acetal means more than one compound of the same structure, and may have different structures so long as two or more compounds of the same structure are present. Further, a cyclic acetal as used herein does not include a cyclic formal compound.

In the process of the invention, polyhydroxyl compounds are reacted with aldehyde compounds to produce a cyclic acetal and a co-product water. The process produces cyclic acetals which are then separated and isolated. The polyhydroxyl compounds may be fed to the distillation column in a first stream, and the aldehyde compounds may be fed to the column in a second stream. Alternatively, the polyhydroxyl compounds and the aldehyde compounds may be fed to the column together as a mixed stream, and the mixed stream may be a single mixed stream fed to the column or two or more mixed streams fed to the column.

The polyhydroxyl compounds have at least two hydroxyl (—OH) functionalities. The polyhydroxyl compounds may contain ether or ester linkages in the longest carbon chain.

Suitable polyhydroxyl compounds for the present invention include, but are not limited to, ethylene glycol, 1,2-propanediol, 1,3-propanediol, 1,4-butanediol, 1,3-butanediol, 1,2-pentanediol, 2,2-dimethyl-1,3-propanediol, diethyleneglycol, and triethyleneglycol, or combinations thereof. Desirably, the polyhydroxyl compound is ethylene glycol, 1,2-propanediol, 1,3-propanediol, 1,4-butanediol, 1,3-butanediol, or combinations thereof.

The aldehyde compounds contain at least one aldehyde functionality. In the present invention, any aldehyde compound may be used.

For example, the aldehyde compound is represented by the formula:

$$R^1HC=O$$

in which $R^1$ is independently $C_1$-$C_{50}$ alkyl, $C_2$-$C_{50}$ alkenyl, aryl-$C_1$-$C_{50}$ alkyl, aryl-$C_2$-$C_{50}$ alkenyl-, or $C_3$-$C_{12}$ cylcoalkyl, and wherein the alkyl, alkenyl, aryl, and cycloalkyl groups of $R^1$ are optionally saturated or unsaturated, and branched or unbranched or substituted or unsubstituted with 1, 2, or 3 groups comprising —OH, halogen, dialkylamino, $C_1$-$C_6$ alkyl, aldehyde, ketone, carboxylic acid, ester, ether, alkynyl, dialkylamide, anhydride, carbonate, epoxide, lactone, lactam, phosphine, silyl, thioether, thiol, aryl, phenol, or combinations thereof.

The aldehyde compound may, if desired, have one aldehyde functional group wherein the aldehyde carbon atom is bonded to a (i) branched or unbranched $C_1$-$C_9$ alkyl group or (ii) an aryl or alicyclic group which is optionally substituted with a branched or unbranched $C_1$-$C_9$ alkyl group.

Examples of an aldehyde compounds include, but are not limited to, benzaldehyde, acetaldehyde, propionaldehyde, butyraldehyde, isobutyraldehyde, pentaldehyde, 2-methylbutyraldehyde, 3-methylbutyraldehyde, n-pentanal, isopentanal, hexaldehyde, heptaldehyde, 2-ethylhexaldehyde, octanal, nonanal, n-decanal, 2-methylundecanal, lauryl aldehyde, myristyl aldehyde, cetyl aldehyde, stearyl aldehyde, behenyl aldehyde, glutaraldehyde, acrolein, crotonaldehyde, oleyl aldehyde, linoleyl aldehyde, linolenyl aldehyde, erucyl aldehyde, cinnamaldehyde, 1,3-cyclohexanedicarboxaldehyde, 1,4-cyclohexanedicarboxaldehyde, and combinations thereof.

In the present invention, a catalyst may optionally be employed. Preferably, a catalyst is present. By a catalyst is meant any compound that initiates or accelerates the reaction between the aldehyde compounds with the polyhydroxyl compound. Desirably the compound selected not only initiates and/or accelerates the reaction, but is also itself not ultimately consumed and can be recovered.

Desirably, a catalyst is present in the distillation reaction zone. The catalyst used is desirably a liquid in the distillation zone. More preferably, the catalyst used is a liquid when introduced into the reactive distillation column.

The first stream or mixed stream comprising polyhydroxyl compounds may also contain an acid catalyst, and such as a catalyst in liquid form inside the column or in the first stream when introduced into the column or when isolated at 25° C. and 1 atmosphere. The first stream or mixed stream may be entirely a liquid stream and desirably a homogeneous liquid stream as introduced into the column. The first stream may comprise liquid polyhydroxyl compound and a liquid catalyst, or a mixed stream may comprise liquid polyhydroxyl compound and a liquid catalyst and liquid aldehyde compounds.

Acids that may be used as catalysts for the production of cyclic acetals in the present invention include any conventional catalyst, such as hydrochloric acid, sulfuric acid, phosphoric acid, hydrofluoric acid, hydrobromic acid, hydroiodic acid, hydroperchloric acid, para-toluene sulfonic acid, methyl sulfonic acid, and the like.

In a preferred embodiment, the catalyst is a compound having one or more phosphorus atoms, and desirably is phosphorous acid or phosphoric acid, and these acids are usually aqueous.

The amount of catalyst is not particularly limited. For example, the amount of catalyst measured as the active atom (e.g. chlorine, sulfur, or phosphorus atoms) may be present in an amount of at least 50 ppmw or at least 100 ppmw, or at least 150 ppmw or at least 200 ppmw and up to 1000 ppmw or up to 750 ppmw or up to 500 ppmw, based on the weight of fed polyhydroxyl compounds.

The production of cyclic acetals is accomplished through the use of a reactive distillation column. The reactive distillation column is vertically oriented. FIG. 1 illustrates an example of a reactive distillation column useful in the process of the invention. In a single distillation column, the reaction of the aldehyde compounds and polyhydroxyl compounds and withdrawal of the reaction mixture containing cyclic acetal compounds occurs.

In FIG. 1, a distillation apparatus 9, (i.e. a column) has three zones: a reaction zone (11), a rectification zone (10), and a stripping zone (12). While the reaction zone in FIG. 1 is illustrated as having discrete boundaries between the stripping zone and the rectification zone, this is for illustration purposes only. The reaction zone is the zone within the distillation column in which a reaction between the aldehyde compounds and the polyhydroxyl compounds takes place. Since such reactions take place throughout the entire internal space within distillation column, including to some extent in the areas concentrated in rectification and stripping, the reaction zone comprises the entire internal volume of the distillation column. Rectification occurs in the rectification zone where lighter boiling compounds are physically concentrated, which is desirably in the upper ½ of the column, while stripping occurs in the stripping zone where heavier boiling compounds are concentrated which is desirably within the lower ½ of the column. As illustrated in FIG. 1, the reaction is concentrated in the middle section 11 of the column, while the rectification and stripping functions are concentrated in zones 10 and 12 respectively. For purposes of convenience, each of these zones will be referred to the reaction zone 11, rectification zone 10, and stripping zone 12 although it is understood that each reaction take place throughout the internal void spaces of the column. The polyhydroxyl compounds are fed into the upper ½ height of the column, and the aldehyde compounds are fed into the lower ½ of the column height as a second stream. In each case as used throughout this description, the column height is measured as the internal void height of the column. For example, the first stream can be introduced at a location within the top ⅓ height of the column, while the second stream can be fed into the lower ⅓ height of the column. The rectification zone and the stripping zone locations can also be within the corresponding heights, that is the stripping zone can be located in the lower ½ height, or lower ⅓ height of the column and the rectification zone can be located in the upper ½ or uppermost ⅓ height of the column.

The column may be configured to have more than one stream feeding the column with polyhydroxyl compounds. The fresh feed of polyhydroxyl compounds in the first stream or any additional streams feeding the column may, if desired, be combined with recycled polyhydroxyl compounds separated from the product stream in subsequent separation steps, or the recycled polyhydroxyl compounds may be fed as a separate stream into the column.

The first stream can be introduced into the column at ambient temperature. Alternatively, the first stream can be pre-heated. The pre-heating temperature may range from above 25° C. to a temperature less than the stripping zone temperature, or to a temperature less than the normal boiling point of any polyhydroxyl compounds in the first stream. In one embodiment, the first stream is preheated to a temperature of at least 40° C., or at least 50° C., or at least 60° C., and up to 135° C., or up to 120° C., or up to 100° C., or up to 90° C. The particular set point temperature selected for the first stream will depend on a number of variables, including the type of polyhydroxyl compound, aldehyde compound, and catalyst selected, the feed rates, the pressure within the column, and the desired temperature gradient between the stripping zone and the rectification zone.

The second stream comprising aldehyde compounds can be fed into the column separately from the first stream. While aldehyde compounds may be present in the first stream, the present invention has at least a second stream comprising aldehyde compounds separately introduced into the column at a position different from the point at which the first stream is introduced. The second feed stream may be introduced into the column through feed line 2 into the lower ½ column height, or into the lower ½ column height.

The cumulative amount of polyhydroxyl compounds and aldehyde compounds fed to the column, whether together as a single mixed stream or as two or more separate streams, are at a molar excess of polyhydroxyl compounds over aldehyde compounds. Selectivity to the cyclic acetal and corresponding yield is improved when using a molar excess of polyhydroxyl compounds. The molar ratio is at a rate such that the molar ratio of polyhydroxyl compounds relative to aldehyde compounds is greater than 1:1, or at least 1.1:1, or at least 1.2:1, or at least 1.5:1, or at least 1.75:1, or at least 2:1, or at least 2.2:1, or at least 2.4:1, or at least 2.5:1, or at least 3:1, or at least 4:1, or at least 5:1, or at least 6:1, and up to 20:1, or up to 10:1, or up to 9:1, or up to 8:1, or up to 7:1, or up to 6:1, or up to 5:1, or up to 4:1. For example, the molar ranges may be 1.1:1-20:1, or 1.2:1-10:1, or 1.5:1-10:1, or 1.75:1-8:1, or 2:1-10:1, or 2.5:1 to 10:1, or 3:1-10:1 in each case, of polyhydroxyl moles to aldehyde moles as fed into the column.

The reactive distillation column is employed to synthesize cyclic compounds, and therefore, fresh feeds of polyhydroxyl compounds and fresh feeds of aldehyde compounds are fed to the column. It is not necessary to feed any cyclic acetal compounds to the column, and in one embodiment, the column is not fed with any fresh feed of cyclic acetal compounds, or not fed with any recycle feed of cyclic acetal compounds, or not fed with any stream containing both fresh feed and recycle feed of cyclic acetal compounds.

The reactive distillation process of the invention desirably employs one distillation column. In one embodiment, the reactive distillation process of the invention does not employ any further distillation for manufacture, recovery and isolation of cyclic acetal compounds.

In another embodiment, the method of the invention comprises reacting a stoichiometric molar excess of a polyhydroxyl compound with an aldehyde compound to obtain a cyclic acetal. In this embodiment, there is provided a process for preparing a cyclic acetal comprising:
  (i) reacting a stoichiometric molar excess of a polyhydroxyl compounds with aldehyde compounds to produce reaction mixture comprising cyclic acetal compounds and unreacted polyhydroxyl compounds, and
  (ii) separating in a distillation column at least a portion of cyclic acetal compounds from the reaction mixture.

Entrainer compounds may also be fed to column to break the water-aldehyde azeotrope. The entrainer compounds can be fed as a separate stream or mixed with the second aldehyde compound stream. The entrainer may form a minimum boiling azeotrope in the column with the co-product water to break the water-aldehyde azeotrope. The water-entrainer azeotrope is used to remove the water from the top of the column through line 3. Any common entrainer may be used that forms an azeotrope with water and examples include pentane, hexane, heptane, octane, benzene, and toluene. The reactive distillation column may be any type of distillation column, including a vacuum distillation column, steam distillation column, or desirably a fractionating column. It may have from 5 to 85 theoretical trays. The column may be configured with trays or packing. The number of actual trays in the column may range from 10 to 85 trays.

The internal configuration of the column is not particularly limited and a wide variety of configurations can be used as known in the art. The column internals can include, but not be limited to, trays, random packing, structured packing, baffles, varying diameters throughout the column, each with or without catalyst. The internal configuration can also be mixed depending on the function of the column section. For example, one may employ trays in one section and structured packing in another section of the column. Means known in the art for increasing the liquid hold up time can also be used. Suitable liquid hold-up times (excluding reboiler) include 1 min to 60 minutes, or 3 min to 10 min.

The process of the invention can be conducted batchwise or as a continuous process, desirably as a continuous process. The reactive distillation column may be run in a steady state, meaning that except for interruptions, start-up or turn-overs, the stream rates and process conditions do not substantially change with the passage of time (such as over the course of one month) during operation, including the feed rate, output stream rates, heating and cooling rates, reflux ratio, temperature, pressure, and stream compositions.

The column of the invention can be operated in the following manner. The aldehyde compounds, and if separate streams are used, the aldehyde compounds from the second stream, are vaporized and travel in an upward direction of the vertical column. The column will have a temperature gradient with the highest temperature being within the stripping zone, or a region of the lowermost ½ height or lowermost ¼ height of the column from the bottom, and the lowest temperature being within the rectification zone, or within a region above ¾ the height of the column from the bottom. The stripping zone contains a liquid reaction mixture. In one embodiment, a liquid product stream can be withdrawn from the liquid reaction mixture. The second stream, as illustrated in FIG. 1, enters the column at a point below the vertical height of the first stream.

The temperature within the column may range from a high temperature of 225° C. to a low temperature of 20° C. at any point within the column.

The stripping zone is heated to a temperature that is above the boiling point of at least one of the aldehyde compounds to ensure that at least a portion of the aldehyde compounds vaporize within the column and travels upward through the column. The stripping zone is heated at a temperature which is effective to allow the product stream withdrawn from the column to be rich in concentration of cyclic acetals by moles relative to the concentration of cyclic acetals in the overhead vapor stream. By rich is meant that the concentration of cyclic acetals in the product stream is higher than the concentration of cyclic acetals in the overhead vapor stream. In another embodiment, the amount of cyclic acetal compounds in the product stream, and if more than one product stream is employed, the cumulative amount of cyclic acetals in all product streams is greater than 50 mole %, or greater than 60 mole %, or greater than 70 mole %, or greater than 80 mole %, or greater than 85 mole %, or greater than 90 mole % cyclic acetals based on the total moles of cyclic acetals withdrawn from the column at all locations. The temperature of the stripping zone is determined by measuring the temperature of the liquids in the lower ¼ height of the column. The temperature can be measured by inserting a thermocouple into the liquid reservoir at the base of the column.

In one embodiment, the temperature of the reaction mixture in the liquid reservoir at the base of the column is within the range of lower than the boiling point of the polyhydroxyl compounds and higher than the boiling point of the cyclic acetal compounds each at the operating pressure in the column. Even though the boiling point of the liquid reaction mixture is higher than the boiling point of the cyclic acetals at operating pressure, cyclic acetals are present in the liquid product stream withdrawn from the column. In one embodiment, the temperature of the reaction mixture is at its boiling point under operating pressures. Suitable temperatures of the liquid reaction mixture at the base of the column are at least 70° C., or at least 80° C., or at least 100° C., or at least 120° C., or at least 130° C., or at least 135° C., or at least 150° C., and up to 200° C., or up to 190° C., or up to 180° C., or up to 175° C. The particular temperature selected will depend at least in part upon the type of aldehydes compounds used, the type of polyhydroxyl compounds used, the type of acetal formed, and the column pressure. For example, the temperature within the stripping zone, or at the lower ¼ height of the column, or within the liquid reaction mixture contacting the base of the column, can range from 100° C. to 180° C., or from 135° C. to 170° C.

The heat to the stripping zone may be supplied by any conventional means, typically a heat exchanger, or reboiler.

The rectification zone in the column is also heated. The source of heat for the rectification zone is desirably the sensible heat generated from the stripping zone, and the temperature in the rectification zone can be controlled by the reflux which cools the vapors in the rectification zone. The reflux rate, number of theoretical plates, and heat input to the stripping zone will largely set the rectification zone temperature and determine the efficiency of the column to separate cyclic acetals from the liquid reaction mixture. The rectification zone temperature can be determined by measuring the temperature of the overhead stream at the exit point of the column, and this temperature is deemed the rectification zone temperature even though it is recognized that there will exist a temperature gradient throughout the column.

The rectification zone temperature is desirable at least 20° C., or at least 25° C., or at least 30° C., or at least 35° C., or at least 40° C., or at least 45° C., or at least 50° C., or at least 55° C., or at least 60° C., or at least 65° C., or at least 70° C., and up to 130° C., or up to 125° C., or up to 120° C., or up to 115° C., or up to 110° C., or up to 105° C., or up to 100° C., or up to 95° C., or up to 90° C., or up to 85° C., or up to 80° C., and in any event, less than the boiling point of at least one type of polyhydroxyl compounds under the column pressure and less than the stripping zone temperature. For example, the rectification zone temperature can be in a range of 55° C. to 90° C., or 60° C. to 85° C., or 65° C. to 80° C.

The distillation column also desirably has a temperature gradient. The vertical temperature gradient within the column may be at least 20° C., or at least 25° C., or at least 30° C., or at least 35° C., or at least 40° C., or at least 45° C., or at least 50° C., or at least 55° C., or at least 60° C., or at least 65° C., or at least 70° C., or at least 75° C., or at least 80° C.

The pressure within the column can range from at least 0.001 atm, or at least 0.2 atm, or at least 0.5 atm, or at least 0.75 atm, or at least 0.85 atm, or at least 0.90 atm, or at least 0.95 atm, or at least 0.98 atm, or about 1 atm, and up to 1.5 atm, or up to 7 atm, or up to 3 atm.

The temperature inside the column at the entry point of the first stream can be lower than the boiling point of at least one polyhydroxyl compound in the first stream. If a mixed stream is used, the temperature at the entry point of the mixed column can be lower than the boiling point of at least one polyhydroxyl compound in the mixed stream. This boiling point is determined at the operating pressure of the column. By maintaining a low temperature at the entry point, the polyhydroxyl compound does not boil at that point under the column pressure and travels downward as a liquid. In one embodiment the liquid polyhydroxyl compounds travel as a liquid down the column for a distance at least through a portion of the reaction zone, or at least a portion of the polyhydroxyl compounds remain a liquid through the distance between the product stream off take and the first stream entry point in the column such that greater than 70 mole % of all unreacted polyhydroxyl compounds are removed from the column as a liquid. In one embodiment, the polyhydroxyl compound flows countercurrent to the aldehyde compound. When the aldehyde compounds and the polyhydroxyl compounds are fed as a mixed stream, they desirably also flow countercurrent during steady state operation such that liquid polyhydroxyl and aldehyde compounds introduced into the column flow down to the bottom of the column and contact vaporous aldehyde compounds flowing up toward the top of the column. The liquid polyhydroxyl compound and the vaporized aldehyde compounds contact each other and react to generate cyclic acetal compounds.

In the reaction zone, the reaction between the polyhydroxyl compounds and the aldehyde compounds form a cyclic acetal compound and water as a co-product. The reaction mixture contains cyclic acetal compounds, and optionally also contains water, and unreacted polyhydroxyl compounds and unreacted aldehyde compounds. At least a portion of the reaction mixture is liquid, and may be present as a liquid phase and a vapor phase in the column. At least a portion of the cyclic acetal compounds in the reaction mixture are also liquid. Optionally, at least a portion of the unreacted polyhydroxyl compounds are also liquid. Optionally, at least a portion of water in the reaction mixture is a vapor and at least a portion of the unreacted aldehyde compounds are a vapor.

Since it is desirable that a molar excess of polyhydroxyl compounds over aldehyde compounds are present in the column, fewer moles of aldehyde are left unreacted in the overhead stream 3 exiting the column than moles of polyhydroxyl compounds left unreacted exiting the column in the liquid product stream, for example at the lower ⅛ height of the column.

The co-product water and unreacted aldehyde compounds, or if an entrainer is used, the water/entrainer/unreacted aldehyde azeotrope is removed in an overhead vapor stream exiting the column preferably at the highest point of the reaction zone within the column. The overhead stream 3 is a vapor and comprises water, unreacted aldehyde compounds, an optional entrainer compound, and minor concentrations of cyclic acetal and polyhydroxyl compounds.

The yield of cyclic acetal compounds (not by-products or water) is determined by dividing the moles of cyclic compounds produced by the moles of acetaldehyde compounds fed, multiplied by 100.

Selectivity to the cyclic acetal is determined by dividing the moles of cyclic acetal compounds produced by the moles of aldehyde compounds converted, multiplied by 100.

Conversion of aldehyde compounds is determined by dividing the moles of aldehyde compounds converted by the moles of aldehyde compounds fed, multiplied by 100.

The process of the invention is capable of producing a cyclic acetal compound yield of at least 90%, or at least 91%, or at least 92%, or at least 93%, or at least 94%, or at least 95%, or at least 96%, or at least 97%, and up to 100%, or up to 99.5%, or up to 99%, or up to 98.5%, or up to 98% based on the amount of aldehyde compounds fed to the reaction zone.

The process of the invention can convert at least 80%, or at least 85%, or at least 90%, or at least 91%, or at least 92%, or at least 93%, or at least 94%, or at least 95%, or at least 96%, or at least 97%, or at least 98%, or at least 99%, and up to 100%, or up to 99.5%, or up to 99% of the aldehyde compounds.

The selectivity to the cyclic acetal compounds can be at least 80%, or at least 85%, or at least 90%, or at least 91%, or at least 92%, or at least 93%, or at least 94%, or at least 95%, or at least 96%, or at least 97%, or at least 98%, or at least 99%, and up to 100%, or up to 99.5%, or up to 99%.

Table 1 below illustrates the composition ranges in mole % of different embodiments in each column for each ingredient in the overhead stream, wherein the stated mole %s are based on the moles of all ingredients within the overhead stream. By ingredients for purposes of determining the quantities in any table is meant the reactants, reaction products, catalysts, solvents or diluents, entrainers, and co-products and by-products and impurities generated from a reaction, that are present in the stream in any state, whether vapor or liquid:

TABLE 1

| Ingredient | E1 mole % | E2 mole % | E3 mole % | E4 mole % |
|---|---|---|---|---|
| Water | 5-90% | 5-50% | 10-50% | 10-30% |
| Unreacted Aldehyde | 0-90% | 25-65% | 0-5% | 70-90% |
| Optional Entrainer | 0-90% | 30-90% | 50-90% | 0% |
| Cyclic Acetals | 0-35% | 0-20% | 0-10% | 0-10% |
| Polyhydroxyl Compounds | 0-1% | 0-0.5% | 0-0.25% | 0-0.25% |

Table 2 below illustrates the distribution of each ingredient to the overhead vapor stream compared to the total amount of the corresponding ingredient in all streams exiting the column with mole % ranges for each ingredient in the overhead vapor stream in any state, wherein the stated mole %s are now based on the cumulative moles of the corresponding ingredient in all streams (e.g. product and overhead vapor) exiting the column:

TABLE 2

| Ingredient | E5 mole % | E6 mole % | E7 mole % |
|---|---|---|---|
| Water | 80-100% | 90-100% | 95-100% |
| Unreacted Aldehyde | 70-100% | 90-100% | 95-100% |
| Optional Entrainer | 80-100% | 90-100% | 95-100% |
| Cyclic Acetals | 0-50% | 0-20% | 0-10% |
| Polyhydroxyl Compounds | 0-10% | 0-5% | 0-1% |

The overhead stream is condensed in a condenser 4. The condensate is collected in receiver or reflux drum 14 and optionally separated by any conventional means, such as decantation, secondary distillation, evaporation, or centrifuge. In a continuous process, the upper phase of the condensate in the receiver 5 is organic rich, is withdrawn, and is returned to the column as reflux. The lower phase of the receiver 6 is water rich, withdrawn from the receiver, and sent to a water treatment facility or further processed.

While the column of the invention can be operated without a reflux, it is preferred to completely reflux the upper phase of the condensate to reach maximum conversion. A portion of the upper phase can be taken off and is desirable if there are impurities or by-products or co-products that prefer the organic phase.

The cyclic acetal compounds formed in the reaction zone of the column will possess a boiling point higher than that of the reacting aldehyde compounds. Most unreacted aldehyde and co-product water and optional entrainer will be removed from the product cyclic acetal in the rectifying zone, 12, and sent upwards in the column and exit the column in the overhead vapor stream. The cyclic acetal product can be removed at a point below the reaction zone as product stream 13.

A product stream is deemed all streams withdrawn from the column that are rich in concentration of cyclic acetal compounds relative to the concentration of acetal compounds present in the overhead vapor stream. The product stream withdrawn from the column can be a liquid or vapor. If a liquid, the product stream is withdrawn from the liquid reaction mixture. If the product stream is withdrawn as a vapor, the column can be configured with one or more vapor sidedraw take-off points. In one embodiment, the column is configured with one product stream and the product stream is a liquid product stream as taken from the column. For example, the cyclic acetal may be removed from the lower ⅛ height of the column, or from the bottom of the base of the column. Unreacted polyhydroxyl compounds also exit the column below reaction zone in the product stream. The product stream comprises cyclic acetal compounds, unreacted polyhydroxyl compounds, and minor or trace concentrations of unreacted aldehyde compounds, catalyst, water and optional entrainer compounds. The majority (e.g. greater than 70 wt. %) of the catalyst employed, if homogeneous, is present in the product stream.

The column may optionally be equipped with a reboiler. The product stream exiting the reactive distillation column at the point described above may feed the reboiler, heated, and a portion returned to the stripping zone of the column and another portion removed from the distillation process altogether for purification and isolation of the cyclic acetal compounds.

The amount of cyclic acetal in the product stream is greater than 50 mole % based on the total moles of cyclic acetals withdrawn from the column at all locations. Preferably, the amount of cyclic acetal in the product stream is at least 60 mole %, or at least 70 mole %, or at least 80 mole %, or at least 85 mole %, or at least 90 mole %, or at least 95 mole %, or at least 96 mole %, or at least 97 mole %, or at least 98 mole %, or at least 99 mole %, each based on the total moles of cyclic acetals withdrawn from the column at all locations.

Table 3 below illustrates the composition ranges in mole % for each ingredient in the product stream(s), wherein the stated mole %s are based on the moles of all ingredients within the cumulative product stream(s):

TABLE 3

| Ingredient | E8 mole % | E9 mole % | E10 mole % |
|---|---|---|---|
| Water | 0-8% | 0-3% | 0-0.5% |
| Unreacted Aldehyde | 0-5% | 0-2% | 0-0.25% |
| Optional Entrainer | 0-5% | 0-2% | 0-0.5% |
| Cyclic Acetals | 10-90% | 25-75% | 50-60% |
| Polyhydroxyl Compounds | 10-90% | 25-75% | 40-50% |
| Catalyst | 0-1% | 0-0.5% | 0-0.1% |

Table 4 below illustrates the distribution of each ingredient to the product stream(s) compared to the total amount of the corresponding ingredient in all streams exiting the column with mole. % ranges for each ingredient in the product stream(s), wherein the stated mole. %s are now based on the cumulative moles of the corresponding ingredient in all streams (e.g. product and overhead vapor) exiting the column:

TABLE 4

| Ingredient | E11 mole % | E12 mole % | E13 mole % |
|---|---|---|---|
| Water | 0-10% | 0-5% | 0-1% |
| Unreacted Aldehyde | 0-10% | 0-5% | 0-1% |
| Optional Entrainer | 0-10% | 0-5% | 0-1% |
| Cyclic Acetals | 70-100% | 80-100% | 95-100% |
| Polyhydroxyl Compounds | 70-100% | 80-100% | 95-100% |
| Catalyst | 85-100% | 90-100% | 95-100% |

Suitable cyclic acetals include any compound having a cyclic acetal moiety. The cyclic acetal moiety produced in the process of the invention has two oxygen atoms single bonded to the same carbon atom in the ring structure. Suitable cyclic acetal moieties include 1,3-dioxolane moieties and dioxane moieties (especially 1,3-dioxane moieties), although larger ring compounds having oxygen atoms in the 1,3 position are also contemplated.

The acetal moiety may be represented by the general formula:

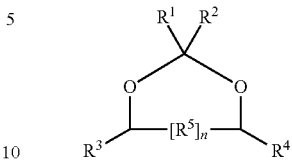

wherein $R^1$, $R^2$, $R^3$, and $R^4$ are independently H; a branched or un-branched $C_1$-$C_{50}$ alkyl, $C_2$-$C_{50}$ alkenyl, aryl-$C_1$-$C_{50}$ alkyl, aryl-$C_2$-$C_{50}$ alkenyl-, $C_3$-$C_{12}$ cylcoalkyl, or a $C_3$-$C_{50}$ carboxylate ester; and wherein the alkyl, alkenyl, aryl, and cycloalkyl groups of $R^1$, $R^2$, $R^3$, and $R^4$ are optionally substituted with 1, 2, or 3 groups independently selected from —OH, halogen, dialkylamino, aldehyde, ketone, carboxylic acid, ester, ether, alkynyl, dialkylamide, anhydride, carbonate, epoxide, lactone, lactam, phosphine, silyl, thioether, thiol, and phenol; and wherein one but not both of $R^1$ or $R^2$ is H; and wherein $R^5$ is branched or unbranched divalent alkyl or divalent alkenyl group each having 1 to 8 carbon atoms and optionally containing 1, 2, or 3 oxygen atoms in the alkyl or alkenyl group; and wherein n is an integer selected from 0 or 1.

$R^1$, $R^2$, $R^3$, and $R^4$ may independently be H, or a branched or un-branched $C_1$-$C_6$ alkyl group. Or, $R^1$, $R^2$, $R^3$, and $R^4$ may independently be H, or a branched or un-branched $C_1$-$C_4$ alkyl group. $R^1$ may be a branched or unbranched $C_1$-$C_6$ alkyl group while $R^2$ is a hydrogen atom.

$R^5$ may be a branched or unbranched divalent alkyl group having 1 to 6, or 1 to 4, or 1 to 3, or 1 to 2 carbon atoms.

Examples of cyclic acetals include 2-propyl-1,3-dioxolane, 2-propyl-1,3-dioxane, 2-ethyl-1,3-dioxolane, 2-ethyl-1,3-dioxane, 2-methyl-1,3-dioxolane, 2-methyl-1,3-dixoane, 2-propyl-4-methyl-1,3-dioxane, 5,5-dimethyl-2-propyl-1,3-dioxane, 5,5-dimethyl-2-ethyl-1,3-dioxane, 2-ethyl-1,3-dioxepane, 2-ethyl-1,3,6-trioxocane. The specific cyclic acetal made depends on the desired end use solvent application. For example, the following cyclic acetals 2-propyl-1,3-dioxolane, 2-propyl-1,3-dioxane, 2-ethyl-1,3-dioxolane, 2-ethyl-1,3-dioxane, 2-methyl-1,3-dioxolane, 2-methyl-1,3-dioxane, 5,5-dimethyl-2-propyl-1,3-dioxane, 2-ethyl-1,3-dioxepane, 2-ethyl-1,3,6-trioxocane are suitable to make their respective solvents ethylene glycol monobutyl ether, 3-butoxy-1-propanol, ethylene glycol monopropyl ether, 3-propoxy-1-propanol, ethylene glycol monoethyl ether, 3-ethoxy-1-propanol, 3-butoxy-2,2-dimethyl-1-propanol, 4-propoxy-1-butanol, and diethylene glycol monobutyl ether through hydrogenolysis.

Desirably, the amount of cyclic acetal in the overhead vapor stream is less than 50 mole % based on the total moles of cyclic acetals withdrawn from the column at all locations. Preferably, the amount of cyclic acetal in the overhead vapor stream is 40 mole % or less, or 20 mole % or less, or 15 mole % or less, or 10 mole % or less, of 5 mole % or less, or 4 mole % or less, or 3 mole % or less, or 2 mole % or less, or 1 mole % or less, each based on the total moles of cyclic acetals withdrawn from the column at all locations.

In one embodiment, the process of the invention is the production of cyclic acetals in a reactive distillation column to a yield of at least 80%, or at least 85%, or at least 87%, or at least 89%, or at least 90%.

Since the process of the invention is to synthesize and isolate cyclic acetal compounds, there is also provided a step to form a separated cyclic acetal stream comprising at least 80 mole %, or at least 85 mole %, or at least 90 mole % or at least 92 mole % or at least 95 mole %, or at least 97 mole % cyclic acetals based on the moles of all ingredients in the separated cyclic acetal stream. This stream is isolated.

The cyclic acetal in the product stream can be separated from the polyhydroxyl compounds by any known method into a separated cyclic acetal stream and a separated polyhydroxyl stream. For example, the cyclic acetal can be separated from the polyhydroxyl compounds by a decanting process, or a decanting centrifuge, or a distillation apparatus. Desirably, the process of the invention comprises only a single distillation column between feed of reactants to separation of the desired product from the product stream, inclusive. The process of the invention makes it simpler to separate the cyclic acetal from the product stream because the cyclic acetal will phase separate as an organic phase from the aqueous phase which contains unreacted polyhydroxyl compounds. Separation of the product though phase separation and withdrawal of the organic layer containing the cyclic acetal product is more cost effective than feeding the product stream to yet another distillation column to separate the cyclic acetal from unreacted polyhydroxyl compounds and water.

Therefore, in another embodiment, the process of the invention further provides for separating cyclic acetal compounds from the product stream without distillation to form a separated cyclic acetal stream. The separated cyclic acetal stream, obtained without distillation techniques once the product stream is removed from the distillation column, contains cyclic acetal compounds in a high concentration with very little loss of cyclic acetals into the separated polyhydroxyl compounds stream.

The reactive distillation process of the invention, including any downstream refining of or separation of any ingredients in the overhead vapor stream or any product stream from the reactive distillation column, desirably does not include equipment operated to hydrolyze the cyclic acetal compounds in the product stream or in the separated cyclic acetal stream. Rather, the process of the invention is operated to synthesize and isolate cyclic acetal compounds. An example of the separated cyclic acetal stream composition, which can be used as a final and isolated cyclic acetal stream or as a crude separated cyclic acetal stream suitable for further refining to purify the composition towards cyclic acetal compounds, is set forth in Tables 5 and 6 below, wherein the mole percentages contained in the separated cyclic acetal stream are based on the moles of all ingredients in the separated cyclic acetal stream in the case of Table 5 and based on the molar amounts of all ingredients in the product stream to be separated in Table 6.

TABLE 5

| Ingredient | E14 mole % | E15 mole % | E16 mole % |
|---|---|---|---|
| Water | 0.0-2 | 0.0-1 | 0.0-0.2 |
| Unreacted Aldehyde | 0.0-5 | 0.0-2 | 0.0-0.25 |
| Optional Entrainer | 0-5 | 0-2 | 0-0.5 |
| Cyclic Acetals | 70-100 | 80-100 | 90-100 |
| Polyhydroxyl Compounds | 0.0-20 | 0.0-15 | 0.0-10 |
| Catalyst | 0-1 | 0-0.5 | 0-0.01 |

TABLE 6

| Ingredient | E17 mole % | E18 mole % | E19 mole % |
|---|---|---|---|
| Water | 0.0-1 | 0-0.5 | 0-0.1 |
| Unreacted Aldehyde | 0.0-2.5 | 0-1 | 0-0.25 |
| Optional Entrainer | 0-2.5 | 0-1 | 0-0.5 |
| Cyclic Acetals | 30-60 | 35-60 | 45-60 |
| Polyhydroxyl Compounds | 0-10 | 0.0-7 | 0-5% |
| Catalyst | 0-0.5 | 0-0.25 | 0-0.05 |

An example of the separated polyhydroxyl compounds stream composition is set forth in Tables 7 and 8 below, wherein the molar percentages are based on all ingredients in the separated polyhydroxyl compounds stream in the case of Table 7 and based on the amount of all ingredients in the product stream to be separated in Table 8.

TABLE 7

| Ingredient | E20 mole % | E21 mole % | E22 mole % |
|---|---|---|---|
| Water | 1-25 | 2-20 | 5-15 |
| Unreacted Aldehyde | 0.0-2 | 0.0-1 | 0-0.3 |
| Optional Entrainer | 0-5 | 0-2 | 0-0.5 |
| Cyclic Acetals | 0-25 | 1-20 | 5-15 |
| Polyhydroxyl Compounds | 60-100 | 70-100 | 80-100 |
| Catalyst | 0.1-0.5 | 0.1-0.5 | 0.1-0.5 |

TABLE 8

| Ingredient | E23 mole % | E24 mole % | E25 mole % |
|---|---|---|---|
| Water | 0.5-15 | 1-10 | 2-8 |
| Unreacted Aldehyde | 0-1 | 0-0.5 | 0-0.15 |
| Optional Entrainer | 0-3 | 0-1 | 0-0.25 |
| Cyclic Acetals | 0-15 | 1-10 | 2-8 |
| Polyhydroxyl Compounds | 10-90 | 25-75 | 35-50 |
| Catalyst | 0.05-0.25 | 0.05-0.25 | 0.05-0.25 |

The separated polyhydroxyl compounds can be recycled to the first stream or separately fed into the column for further use as a reactant.

It is also preferred to select a catalyst which is miscible in the polyhydroxyl compounds and immiscible with the cyclic acetal compounds. In this way, the catalyst is contained in the polyhydroxyl phase and removed from the product stream along with the polyhydroxyl phase in the separated polyhydroxyl stream, thereby eliminating extensive neutralization of the cyclic acetal prior to use. This aspect of the invention also allows for convenient recycle of the excess diol and acid catalyst in the separated polyhydroxyl stream to the column.

The cyclic acetal compounds in the separated cyclic acetal stream can be converted through hydrogenolysis to provide the corresponding ether alcohol solvents.

WORKING EXAMPLES

The following apparatus was used for Examples 1-8. A 1" glass distillation column packed with protruded stainless steel packing was assembled. The column was constructed of three 16" zones. The bottom (representing a stripping zone) and middle zones (representing a reaction zone) were separated by a feed plate. To this feed plate was attached a feed line and a pump through which aldehyde was delivered to the column. The feed plate was attached at the $10^{th}$ theoretical tray. The middle and top zones (representing a rectification zone) were joined by a second feed plate. A feed line and pump were connected to this plate through which polyhydroxyl compound and acid catalyst were delivered to the $22^{nd}$ theoretical tray. The feed line was connected to a pre-heater that was attached directly to the feed plate. The polyhydroxyl compound/acid catalyst mixture was preheated to 70° C. prior to entering the column. The temperature in the preheater was controlled by means of a thermowatch connected to a glass thermometer immersed in the polyhydroxyl compound/acid mixture.

A Dean-Stark trap to which was attached a glycol chilled condenser was coupled to the top of the column. The overhead stream from the column comprised of an aldehyde/acetal/water azeotrope was condensed and separated in the trap. The top organic aldehyde/acetal phase was continuously returned to the column while the bottom water rich phase was periodically removed from the trap and discarded. The Dean-Stark trap also contained a thermowell and thermometer which were placed before the condenser.

The bottom zone of the column was attached to the middle joint of a 3 L, three-necked round bottom which served as a base pot. The basepot was placed in an electric heating mantle which was controlled by an adjustable thermostat. A thermowell and thermometer were connected to the base pot in a second neck. A sample thief (long, thin glass tube with a condenser attached to a pump) was connected to the third neck. The sample thief was connected to a second glycol chilled condenser and a takeoff line and pump. The pump was used to remove product from the base pot throughout the course of the experiment.

For all examples, a mixture of polyhydroxyl compound (300 g) and water (100 g) was added to the basepot at start up. The mixture was heated until the water began to condense into the Dean-Stark trap at the top of the column. In this way, the column was heated from base to top to 100° C. At this point, the aldehyde and polyhydroxyl compound feeds were begun.

Examples 1-4

Synthesis of 2-propyl-1,3-dioxolane

Examples 1-4 were carried out using the apparatus described above. Prior to each example, the column was heated to 100° C. with boiling water as described above. Normal butyraldehyde was fed through the bottom feed plate and a mixture of ethylene glycol and 500 ppmw phosphoric acid (based on the weight of fed ethylene glycol) was fed through the upper feed plate at rates described in Table I. A butyraldehyde/water/acetal azeotrope was condensed overhead at 72° C. The basepot reached a maximum temperature of 140° C. Material was removed from the basepot throughout the run. The material separated into two phases, each of which was analyzed by gas chromatography. The results are listed in Table I.

TABLE I

Synthesis of 2-propyl-1,3-dioxolane

| EXAMPLE | 1 | 2 | 3 | Comp. Ex. |
|---|---|---|---|---|
| EG Feed Rate (g/min) | 2.9 | 2.6 | 2.9 | 1.5 |
| Butyraldehyde Feed Rate (g/min) | 1.7 | 1.3 | 2.2 | 3.9 |

TABLE I-continued

Synthesis of 2-propyl-1,3-dioxolane

| EXAMPLE | 1 | 2 | 3 | Comp. Ex. |
|---|---|---|---|---|
| EG:CHO (mol:mol) | 2.0 | 2.5 | 1.5 | 0.5 |
| Basepot Temperature (° C.) | 138 | 138 | 119 | 114 |
| Total Feed Time (min) | 480 | 575 | 780 | 420 |
| Bottoms Removed (g) | 1390 | 992 | 3371 | 1337 |
| Bottoms Upper Phase (g) | 530 | 566 | 1959 | 1337 |
| 2-propyl-1,3-dioxolane(wt %) | 100% | 100% | 96% | 41% |
| EG(wt %) | 0% | 0% | 0.25% | 10% |
| Water(wt %) | 0% | 0% | 1.3% | 1.6% |
| Butyraldehyde(wt %) | 0% | 0% | 2.4% | 47% |
| 2-propyl-1,3-dioxolane(mol %) | 100% | 100% | 88% | 28% |
| EG(mol %) | 0% | 0% | 0.43% | 13% |
| Water(mol %) | 0% | 0% | 7.7% | 7.1% |
| Butyraldehyde(mol %) | 0% | 0% | 3.6% | 52% |
| Bottoms Lower phase (g) | 860 | 426 | 1412 | 0 |
| 2-propyl-1,3-dioxolane(wt %) | 9.4% | 11% | 10% | n/a |
| EG(wt %) | 88% | 86% | 83% | n/a |
| Water(wt %) | 2.6% | 3.0% | 6.0% | n/a |
| Butyraldehyde(wt %) | 0% | 0% | 1.5% | n/a |
| 2-propyl-1,3-dioxolane(mol %) | 4.9% | 5.8% | 4.8% | n/a |
| EG(mol %) | 86% | 84% | 75% | n/a |
| Water(mol %) | 8.8% | 10% | 19% | n/a |
| Butyraldehyde(mol %) | 0% | 0% | 1.2% | n/a |
| Yield PDX* Conversion Selectivity | 82% | 85% | 83% | 58% |

*PDX is the cyclic acetal 2-propyl-1,3-dioxolane

In Comparative Example in the above table, the PDX yield was 58% and the molar ratio of EG:CHO was 0.5:1. Further, the water and EG remained in the same phase making it more difficult to separate the PDX product from the product stream.

Examples 5-7

Synthesis of 2-propyl-1,3-dioxane

Examples 5-7 were carried out using the apparatus described above. Prior to each example, the column was heated to 100° C. with boiling water as described above. Butyraldehyde was fed through the bottom feed plate and a mixture of 1,3-propanediol and 500 ppmw phosphoric acid was fed through the upper feed plate at rates described in Table II. A butyraldehyde/water azeotrope was condensed overhead at 73° C. The basepot reached a maximum temperature of 165° C. Material was removed from the basepot throughout the run. The material separated into two phases, each of which was analyzed by gas chromatography. The results are listed in Table II.

TABLE II

Synthesis of 2-propyl-1,3-dioxane

| EXAMPLE | 5 | 6 | 7 |
|---|---|---|---|
| 1,3-propanediol Feed Rate (g/min) | 2.6 | 2.4 | 2.9 |
| Butyraldehyde Feed Rate (g/min) | 1.3 | 1.5 | 1.1 |
| Diol:CHO (mol:mol) | 2.0 | 1.5 | 2.6 |
| Basepot Temperature (° C.) | 167 | 138 | 160 |
| Total Feed Time (min) | 820 | 675 | 930 |
| Bottoms Removed (g) | 2147 | 1602 | 2922 |
| Bottoms Upper Phase (g) | 660 | 893 | 720 |
| 2-propyl-1,3-dioxane(wt %) | 98% | 97% | 98% |
| 1,3-propanediol(wt %) | 2% | 2.2% | 1.7% |
| Water(wt %) | 0% | 0.13% | 0.17% |

TABLE II-continued

Synthesis of 2-propyl-1,3-dioxane

| EXAMPLE | 5 | 6 | 7 |
|---|---|---|---|
| Butyraldehyde(wt %) | 0% | 0.76% | 0% |
| 2-propyl-1,3-dioxane(mol %) | 97% | 94% | 96% |
| 1,3-propanediol(mol %) | 3.4% | 3.7% | 2.8% |
| Water(mol %) | 0% | 0.9% | 1.2% |
| Butyraldehyde(mol %) | 0% | 1.3% | 0% |
| Bottoms Lower phase (g) | 1487 | 856 | 2202 |
| 2-propyl-1,3-dioxolane(wt %) | 14% | 19% | 14% |
| 1,3-propanediol(wt %) | 85.8% | 79% | 85.5% |
| Water(wt %) | 0.25% | 0.56% | 0.56% |
| Butyraldehyde(wt %) | 0% | 1.4% | 0% |
| 2-propyl-1,3-dioxane(mol %) | 8.6% | 12% | 8.5% |
| 1,3-propanediol(mol %) | 90% | 84% | 89% |
| Water(mol %) | 1.1% | 2.5% | 2.5% |
| Butyraldehyde(mol %) | 0% | 1.6% | 0% |
| Yield Dioxane** Conversion Selectivity | 83% | 81% | 75% |

**2-propyl-1,3-dioxane

Examples 8-9

Synthesis of 4-methyl-propyl-1,3-dioxane

Examples 8-9 were carried out using the apparatus described above. Prior to each example, the column was heated to 100° C. with boiling water as described above. Butyraldehyde was fed through the bottom feed plate and a mixture of 1,2-propanediol (propylene glycol) and 500 ppmw phosphoric acid was fed through the upper feed plate at rates described in Table III. A butyraldehyde/water azeotrope was condensed overhead at 72° C. The basepot reached a maximum temperature of 160° C. Material was removed from the basepot throughout the run which was analyzed by gas chromatography. Unlike the other cyclic acetals, 4-methyl-2-propyl-1,3-dioxane did not separate from propylene glycol. The results are listed in Table III.

TABLE III

Synthesis of 4-methyl-2-propyl-1,3-dioxane

| EXAMPLE | 8 | 9 |
|---|---|---|
| PG Feed Rate (g/min) | 2.4 | 2.5 |
| Butyraldehyde Feed Rate (g/min) | 1.5 | 1.1 |
| PG:CHO (mol:mol) | 1.5 | 2.2 |
| Basepot Temperature (° C.) | 140 | 160 |
| Total Feed Time (min) | 425 | 398 |
| Bottoms Base Material Removed (g) | 1670 | 1487 |
| 4-methyl-2-propyl-1,3-dioxane(wt %) | 49% | 42% |
| PG(wt %) | 45% | 56% |
| Water(wt %) | 0.63% | 1.2% |
| Butyraldehyde(wt %) | 5.7% | 1.0% |
| 4-methyl-2-propyl-1,3-dioxane(mol %) | 35% | 28% |
| PG(mol %) | 55% | 65% |
| Water(mol %) | 3.2% | 5.9% |
| Butyraldehyde(mol %) | 7.3% | 1.2% |
| Yield Dioxane*** Conversion Selectivity | 71% | 86% |

***4-methyl-2-propyl-1,3-dioxane

Comparative Example 1

Synthesis of 2-propyl-1,3-dioxolane

This example illustrates the limitations of conventional synthesis methods. A 250 mL round bottom was charged with 101 g normal butyraldehyde, 44 g of ethylene glycol, and 4 drops 85% phosphoric acid. The round bottom was fitted with a Dean-Stark trap and condenser and the entire apparatus was placed into an electric heating mantle and brought to reflux. The aldehyde/water azeotrope condensed and separated into the trap. Heating was maintained until 13 mL of water had evolved (1 hr). The mixture was cooled and poured into a separatory funnel. The solution was washed twice with 50 mL of saturated sodium bicarbonate solution and once with 50 mL of distilled water. The organics were dried over $MgSO_4$ to yield 82.7 g of material. This solution was fractionally distilled. The fraction at 132° C. was 2-propyl-1,3-dioxolane of which 57.9 g was recovered. This corresponds to a 74% yield, lower than the yields reported in working examples 1-3 in Table I.

Comparative Example 2

Synthesis of 2-propyl-1,3-dioxane

This example illustrates the limitations of conventional synthesis methods. A 500 mL round bottom was charged with 191 g normal butyraldehyde, 101 g of 1,3-propanediol, and 4 drops 85% phosphoric acid. The round bottom was fitted with a Dean-Stark trap and condenser and the entire apparatus was placed into an electric heating mantle and brought to reflux. The aldehyde/water azeotrope condensed and separated into the trap. Heating was maintained until 24 mL of water had evolved (1 hr). The mixture was cooled and poured into a separatory funnel. The solution was washed twice with 50 mL of saturated sodium bicarbonate solution and once with 50 mL of distilled water. The organics were dried over $MgSO_4$ and the residue distilled. A fraction collected at 150° C. was 99.6% acetal and had a mass of 95.7 g. This corresponds to a yield of 56%, lower than the yields reported in Table II.

What we claim is:

1. A liquid composition comprising water in an amount from 0 to 8 mole %, aldehyde compounds in an amount from 0 to 5 mole %, cyclic acetal compounds in an amount from 25 mole % to 75 mole %, polyhydroxyl compounds in an amount from 25 mole % to 75 mole %, and a catalyst in an amount from 0-0.5 mole %, wherein the stated mole percentages are based on the moles of all ingredients within the liquid composition.

2. A liquid composition comprising water in an amount from 0 to 0.5 mole %, aldehyde compounds in an amount from 0 to 0.25 mole %, cyclic acetal compounds in an amount from 50 mole % to 60 mole %, polyhydroxyl compounds in an amount from 40 mole % to 50 mole %, and catalyst in an amount from 0-0.1 mole %, wherein the stated mole percentages are based on the moles of all ingredients within the liquid composition.

3. The composition according to claim 1, which comprises water in an amount of 0 to 3 mole %.

4. The composition according to claim 1, which comprises aldehyde compounds in an amount of 0 to 2 mole %.

* * * * *